United States Patent [19]

Rosenblum

[11] Patent Number: 4,976,688

[45] Date of Patent: Dec. 11, 1990

[54] POSITION-ADJUSTABLE THORACIC CATHETER

[76] Inventor: Jeffrey L. Rosenblum, 180 Barlow Dr. South, Brooklyn, N.Y. 11234

[21] Appl. No.: 306,509

[22] Filed: Feb. 3, 1989

[51] Int. Cl.$^5$ ............................................. A61M 37/00
[52] U.S. Cl. ........................................ 604/95; 604/282
[58] Field of Search .................. 604/93, 95, 264, 280, 604/282, 159, 170, 270; 128/4, 6–8, 207.14, 207.15, 200.26, 348.1, 356; 15/104.33

[56] References Cited

U.S. PATENT DOCUMENTS

| Re. 25,788 | 6/1965 | Sheridan . | |
|---|---|---|---|
| 1,397,732 | 11/1921 | Goodloe | 128/7 |
| 3,190,290 | 6/1965 | Alley et al. . | |
| 3,295,527 | 1/1967 | Alley et al. . | |
| 3,452,740 | 7/1969 | Muller | 604/95 X |
| 3,470,876 | 10/1969 | Barchilon | 604/95 |
| 3,521,620 | 7/1970 | Cook | 604/95 X |
| 3,605,725 | 9/1971 | Benton | 604/95 X |
| 4,682,599 | 7/1987 | Konomura | 128/328 |
| 4,685,457 | 8/1987 | Donenfeld | 128/207.14 |
| 4,753,223 | 6/1988 | Bremer | 128/4 |
| 4,796,007 | 1/1989 | Allred, III et al. | 128/4 |

FOREIGN PATENT DOCUMENTS 1213571  3/1966  Fed. Rep. of Germany ........ 604/95

OTHER PUBLICATIONS

Smith, G. A. et al., "Preliminary Report on a New Method of Intestinal Intubation with the Aid of a Flexible Stylet with Controllable Tip", *Surgery*, vol. 27, issue 6, pp. 817–818 (6/50).

Frumkin, Chapter 6, "*Tube Thoracostomy*", of Roberts and Hedges, *Clinical Procedures in Emergency Medicine*, (W. B. Saunders Company, 1985).

*Primary Examiner*—John D. Yasko
*Assistant Examiner*—Adam J. Cermak
*Attorney, Agent, or Firm*—Bryan, Cave, McPheeters & McRoberts

[57] ABSTRACT

A flexible catheter having an integral curvature control mechanism is disclosed. This mechanism allows the curvature of the catheter to be changed while at least part of the catheter is in a patient, thereby facilitating positioning of the catheter within the patient.

12 Claims, 6 Drawing Sheets

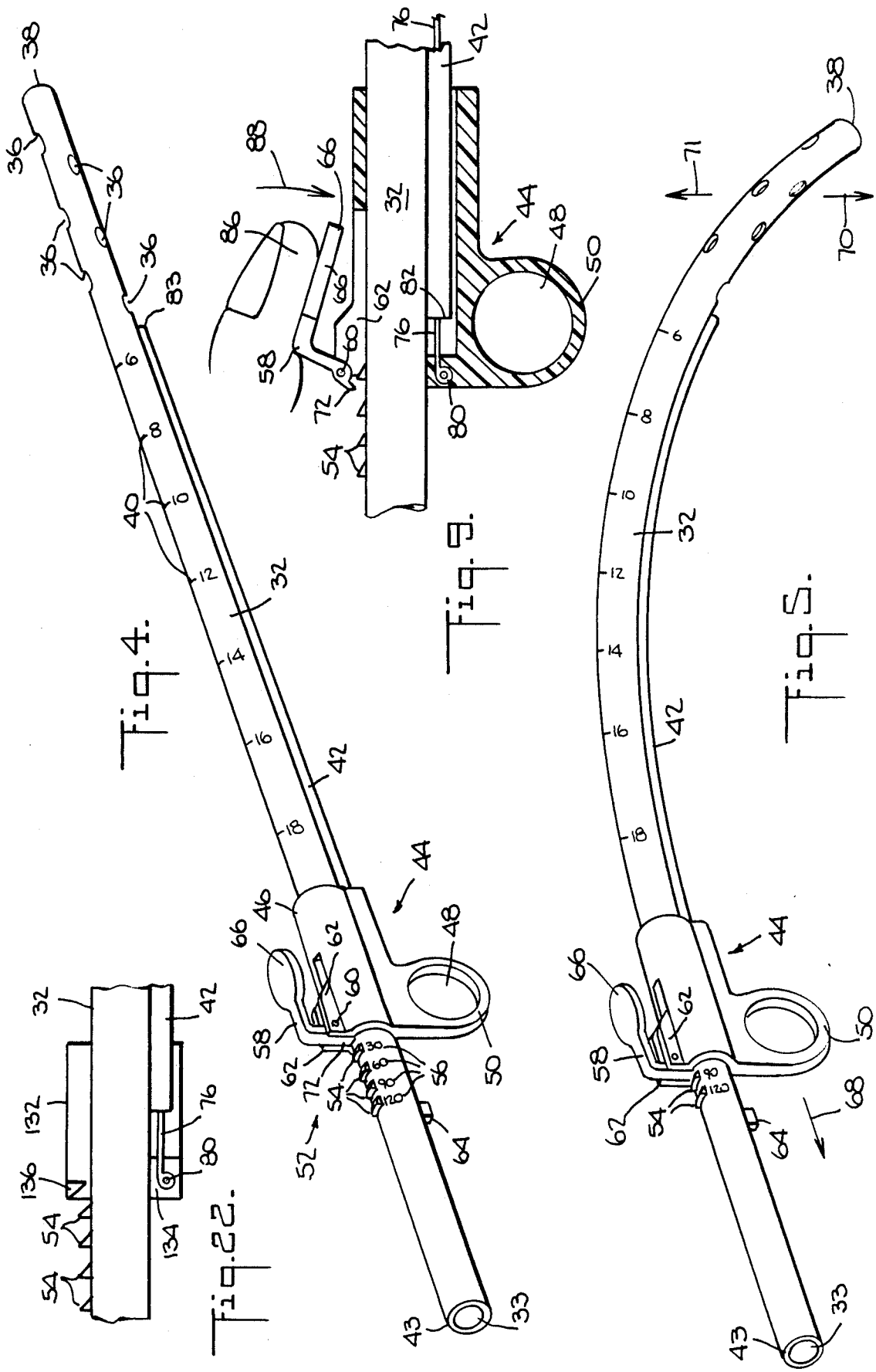

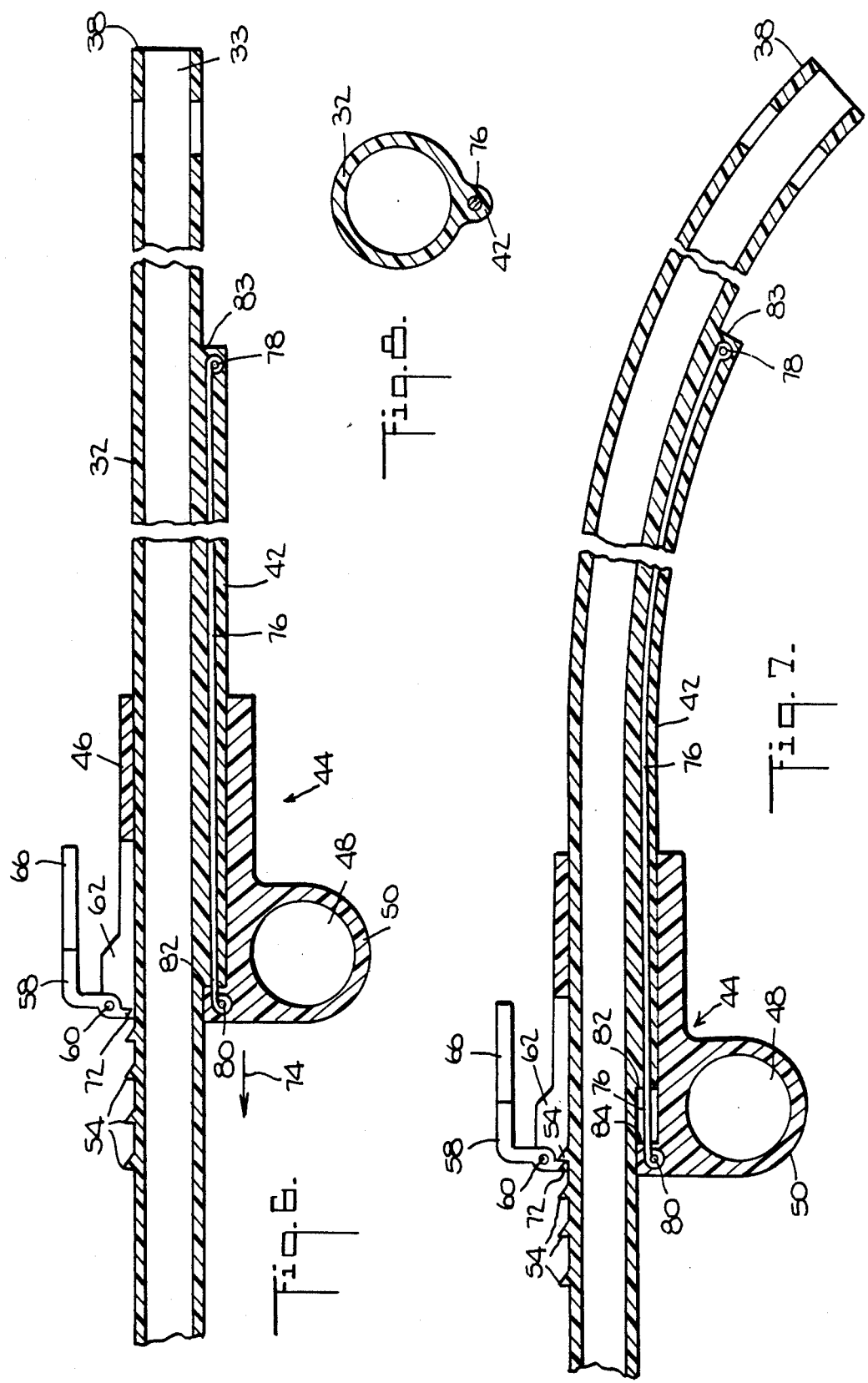

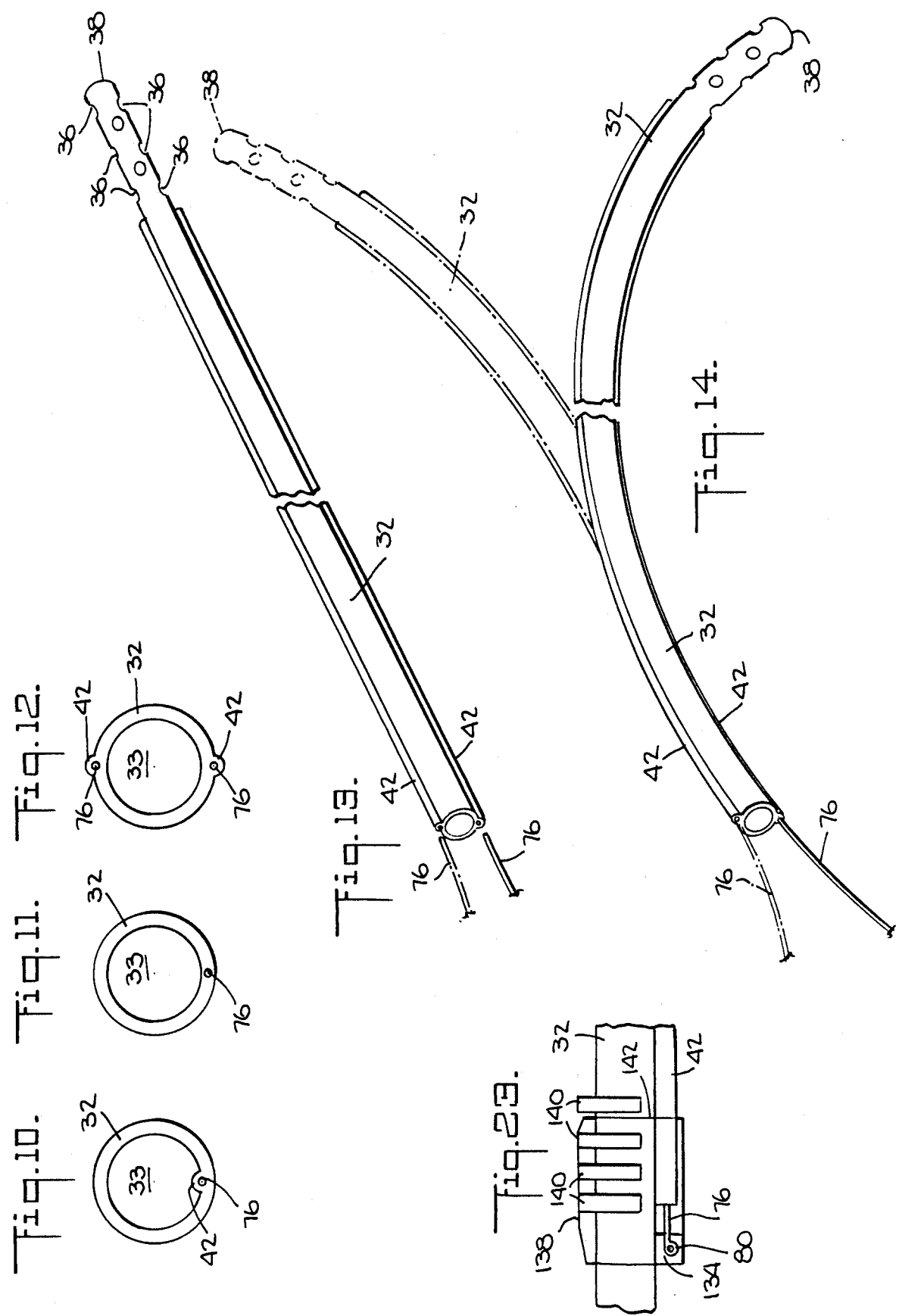

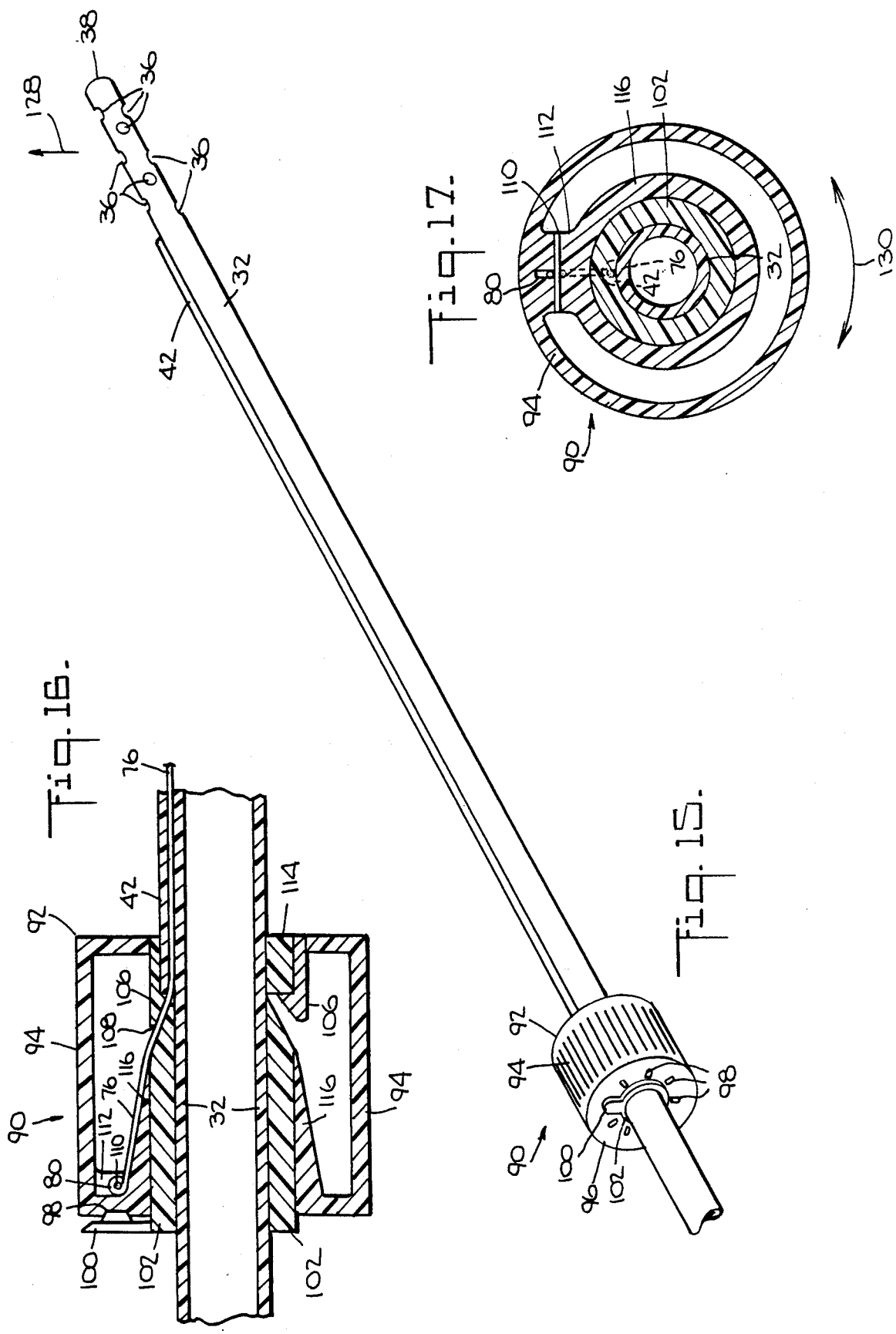

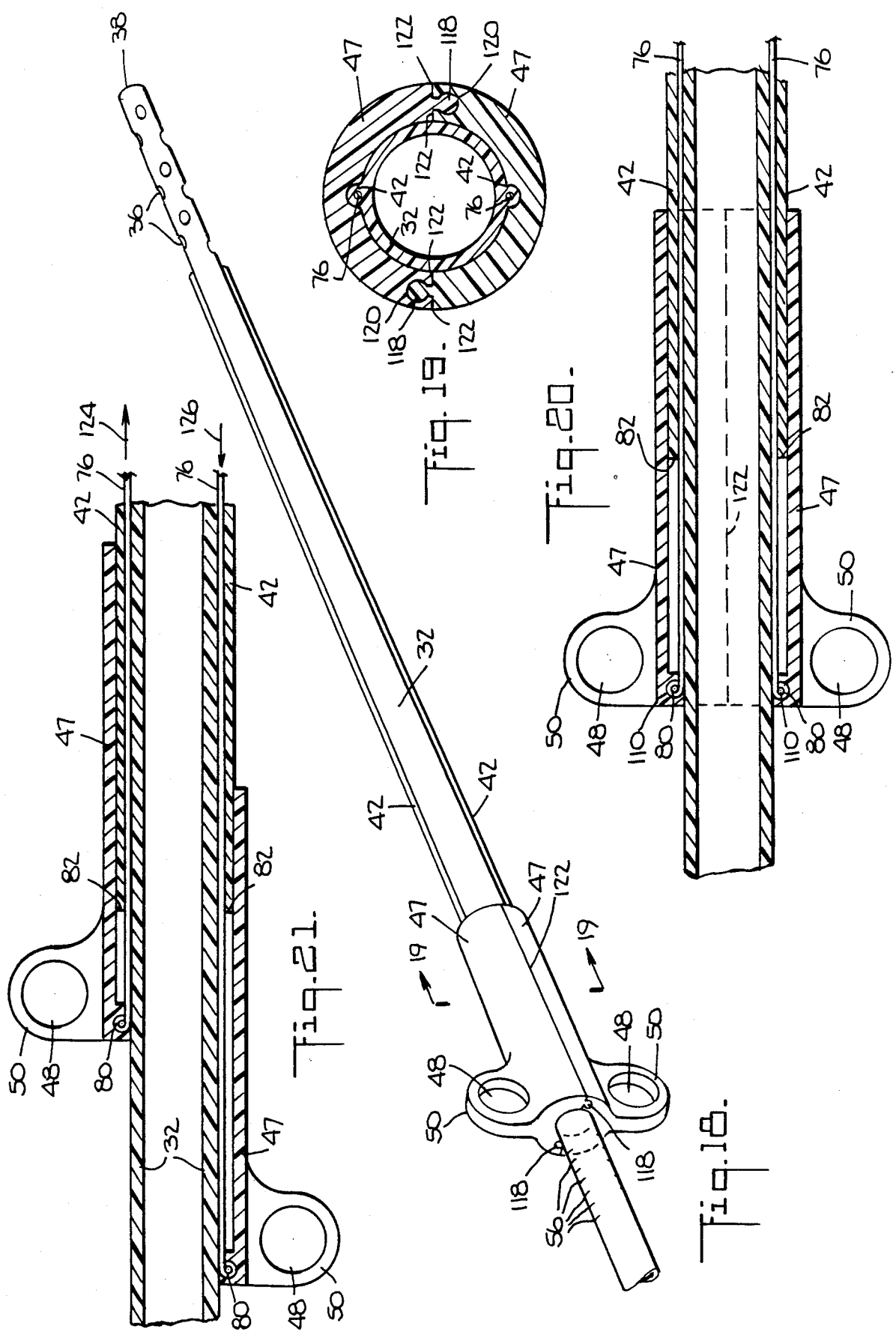

POSITION-ADJUSTABLE THORACIC CATHETER

BACKGROUND OF THE INVENTION

This invention relates to the medical field and more particularly to catheters.

Catheters are used in the medical field to introduce fluids (i.e., liquids and gases) to and to remove fluids from patients. The size (length and diameter), material of construction, and features (e.g., size and location of drainage holes) of a catheter will vary depending on where the catheter is to be inserted, the fluid being carried by the catheter, and the size of the patient. Catheters and their use are described in U.S. Pat. Nos. 3,190,290, 3,295,527, and Re.25,788 and in Chapter 6, Frumkin, "Tube Thoracostomy," of Roberts and Hedges, *Clinical Procedures in Emergency Medicine* (W.B. Saunders Company, 1985), all of which documents are hereby incorporated by reference.

A continuing problem with the use of catheters is properly positioning them in the patient, for example, in the pleural cavity. If a thoracic catheter is to be used to remove gas from the pleural cavity, the distal (far) end of the catheter, which is inserted into the patient, is directed towards the top (apex) of the cavity (as shown in FIGS. 1 and 2). If liquid is to be removed, the distal end is directed downward towards the bottom of the pleural cavity.

The usual procedure for inserting and positioning the catheter involves making an incision between the appropriate ribs and pushing the catheter into the pleural cavity using a clamp (e.g., a Kelly clamp), which is inserted into the same opening as that through which the catheter passes. The clamp also helps direct the catheter to a superior (higher) or inferior (lower) position.

It would be advantageous if the catheter, which is flexible, could itself change its curvature before or after insertion to point in either an up or down direction and maintain that curvature while the catheter is in the patient. That would facilitate positioning of the catheter, would reduce the chance of misdirecting the catheter into adjoining body structures, and would help the catheter maintain its position while it is in the patient.

SUMMARY OF THE INVENTION

A relatively inexpensive catheter capable of changing its curvature before or after insertion into the patient has now been developed. The catheter has all the advantages noted above as well as others that will be apparent to those skilled in the art. The catheter of this invention is in contrast to known medical devices such as the flexible cystoscope, the flexible sigmoidoscope, and the colonoscope, all of which are significantly more expensive than the catheter of this invention and do not change their curvature along a substantial part of their length but can only change the direction of at most their leading 25-75 millimeters.

Broadly, the catheter of this invention comprises an elongate flexible tube for the passage of fluid into or out of a patient, the tube having a wall, a distal end for insertion into the patient, and a proximal end that remains outside the patient, the catheter also comprising control means for changing the curvature of the tube along a substantial portion of its length to facilitate positioning of the tube in the Patient. By "a substantial portion of its length" is meant at least 40%, usually at least 60%, desirably at least 80%, and preferably about 100% of the maximum length of the catheter meant to be inserted into the patient under normal conditions.

In preferred embodiments the proximal ends of one or more control wires are connected to the control means and the distal ends of the wires are connected to the tube towards the distal end of the tube. Pulling the Proximal end of the wire towards the proximal end of the tube pulls the distal end of the wire and thus the distal end of the tube towards the proximal end of the tube, thereby changing the curvature of the tube. The control means may comprise one or more members that ride on the tube and slide or rotate with respect to the tube.

BRIEF DESCRIPTION OF THE DRAWINGS

To facilitate further discussion of the invention, the following drawings are provided in which:

FIG. 4 is a perspective view of a catheter of this invention;

FIG. 5 shows the device of FIG. 4 in which the slidable control means has been moved back towards the proximal end of the device and as a result, the distal end of the device has been moved downward and the curvature along a substantial portion of the device has changed;

FIG. 6 is a longitudinal sectional view of the device of FIG. 4;

FIG. 7 is a longitudinal sectional view of the device showing the distal end of the tube moved downward;

FIG. 8 is a transverse sectional view of the device;

FIG. 9 is a detail view showing the pawl of a ratchet system being released to allow the control means to be moved to reduce the curvature of the tube;

FIGS. 10-12 are transverse sectional views of different embodiments of the catheter of this invention showing different locations for the control wires;

FIG. 13 is a partial view of a catheter of this invention having two control wires;

FIG. 14 shows the catheter of FIG. 13 in two different positions;

FIG. 15 shows another catheter of this invention in which rotatable control means are used to pull the control wire and change the curvature of the tube;

FIG. 16 is a detail longitudinal sectional view of the control means of the catheter of FIG. 15;

FIG. 17 is a transverse sectional view of the control means of FIG. 16;

FIG. 18 is a perspective view of another embodiment of the invention in which two control wires are used;

FIG. 19 is a transverse sectional view taken along line 19—19 of FIG. 18;

FIG. 20 is a detail view of the control means of the device of FIG. 18;

FIG. 21 is a detail view similar to that of FIG. 20 showing the two-part control means slid apart to change the curvature of the catheter;

FIG. 22 is a detail view of the control means of another embodiment; and

FIG. 23 is a detail view of the control means of a preferred embodiment.

DETAILED DESCRIPTION OF THE INVENTION

Figure 1:
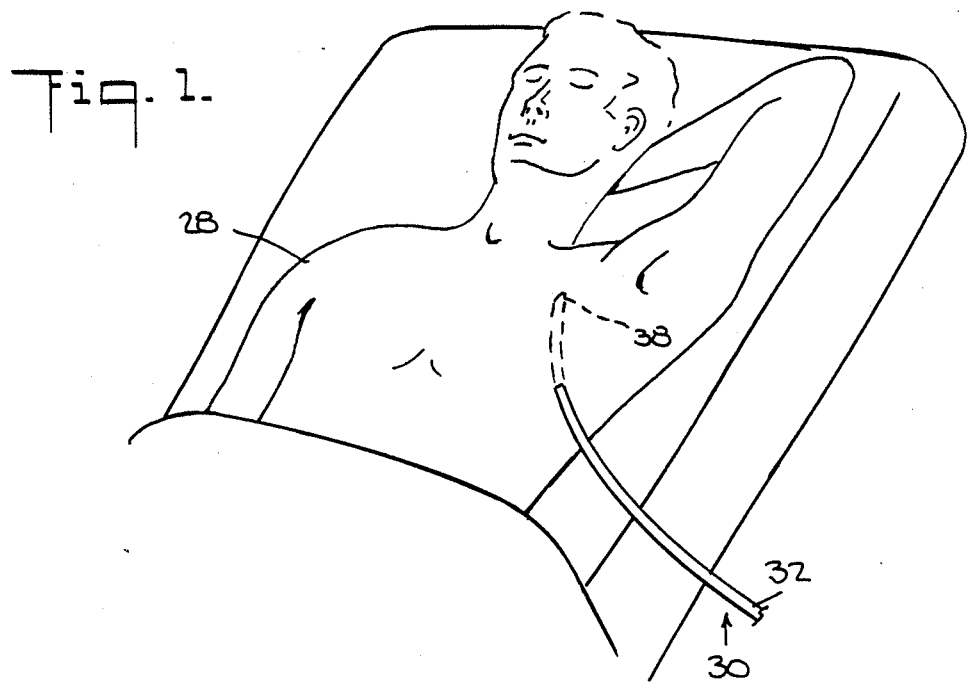
FIG. 1 shows a reclining patient in whom a chest catheter has been inserted with its distal end located towards the apex of the pleural cavity.
Figure 2:
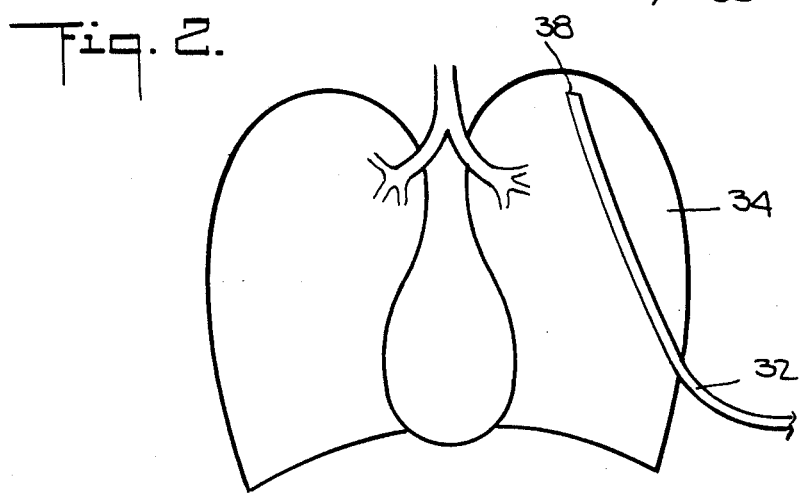
FIG. 2 schematically shows the catheter of FIG. 1 in the pleural cavity.
Figure 3:
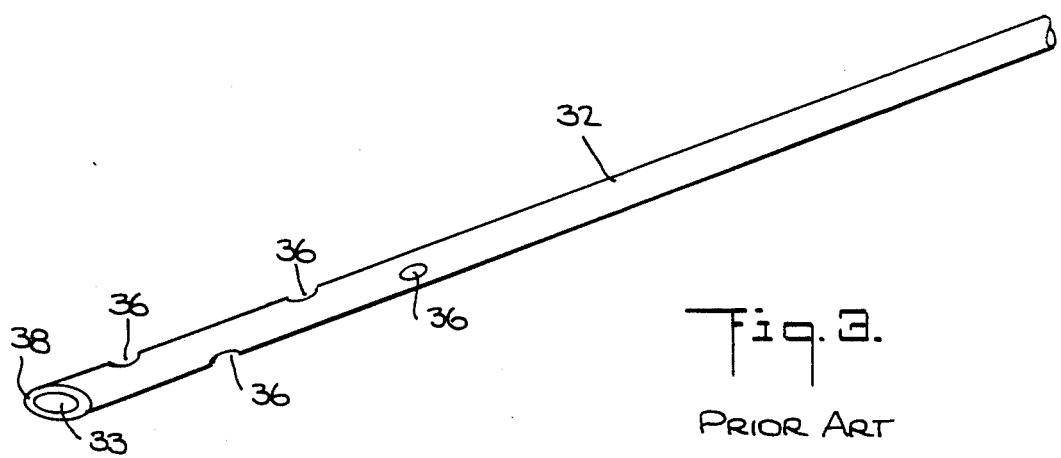
FIG. 3 shows a prior art flexible catheter, which has no integral means for changing its curvature.

FIG. 1 shows a partially reclining patient 28 in whom catheter 30 comprising wall 32 has been inserted. As is well known, such insertion into the pleural cavity is usually made with distal end 38 oriented upward towards the apex of the cavity (as is shown in FIG. 1) or downward towards the bottom of the pleural cavity, for example, for draining fluid (not shown). FIG. 2 schematically shows the catheter in the pleural cavity oriented towards the apex. FIG. 3 shows the typical prior art catheter, comprising an elongate hollow tube having wall 32, a bias-cut distal end 38, hollow passageway 33, and a plurality of openings 36 in wall 32. To prevent air leaks, the catheter is inserted far enough into the patient so that all openings 36 are inside the patient.

FIG. 4 shows one embodiment of the catheter of this invention. This catheter comprises wall 32 having distal end 38, openings 36, and proximal end 43. As with prior art catheters, indicia 40 indicate to the health professional how much of the catheter (usually measured in centimeters) has been inserted into the patient. In contrast to the prior art, the catheter of this invention also comprises gutter 42, which contains control wire 76 (FIG. 9), and control means 44, which in this embodiment comprises a slidable handle.

With respect to FIGS. 4, 5, 6, 7, and 8, slidable handle 44 comprises body 46, curved handle portion 50 defining finger hole 48, and two ears 62. Pawl 58 is rotatably mounted between the two ears 62 by pin 60. Pawl 58 comprises enlarged upper end 66 and lower engaging end 72, which engages ratchet means 52. Ratchet means 52 comprises four teeth 54, each having a triangular cross-section, and angle indicia 56.

Proximal end 80 of control wire 76 is connected to the rear end of handle 44, and distal end 78 of wire 76 is connected to distal end 83 of the gutter towards distal end 38 of the catheter. Control wire 76 can for almost all of its length slide within gutter 42. As handle 44 is pulled in the direction shown by arrow 68 (FIG. 5) towards proximal end 42 of the catheter, distal end 78 of the wire is pulled towards the proximal end of the catheter, thereby pulling distal end 83 of the gutter and distal end 38 of the catheter downward in the direction shown by arrow 70 (FIG. 5) towards proximal end 43 of the catheter. As shown in FIG. 5, that changes the curvature of the catheter along essentially the entire length that can be inserted into a patient under normal conditions, that is, up to the "18" indicia (FIG. 5). Distal end 83 of the gutter is closed so that no fluid can enter the gutter. The only opening into the gutter is at its proximal end 82, where control wire 76 emerges (FIG. 9).

As the slidable handle is pulled back in the direction shown by arrow 74 (FIG. 6), the inclined face of lower engaging end 72 of pawl 58 slides on the forward-facing inclined face of first (right-most) tooth 54 (FIG. 6) and then up and over the tooth to the Position shown in FIG. 7. The normal resilience of the tube fights the change in its curvature caused by the pulling of control wire 76. Were it not for the abutment of the vertical portion of lower engaging end 72 against the vertical face of first inclined tooth 54 (FIG. 7), the resilience of the tube and its natural tendency to become straight would pull slidable handle 44 forward (towards distal end 38), thereby reducing the curvature of (that is, straightening) the tube.

Slidable handle 44 may be pulled back still further towards the proximal end of the catheter to bring lower engaging end 72 up and over second inclined tooth 54, as shown in FIG. 5. The indicia next to each inclined tooth (reference numeral 56 in FIG. 4) indicate the approximate curvature of the catheter in degrees when the handle has been pulled back to engage the corresponding tooth. Handle 44 is prevented from being pulled back too far towards proximal end 43 by stop 64. Similarly, handle 44 can not be slid forward towards distal end 38 too far because inner face 84 (FIG. 7) at some point hits and is stopped by proximal end 82 of gutter 42, as in FIG. 6.

To release pawl 58 from ratchet teeth 54, enlarged upper end 66 of pawl 58 is depressed in the direction shown by arrow 88 (FIG. 9) as by fingertip 86. That rotates pawl 58 clockwise around pin 60, thereby bringing lower engaging end 72 up and moving it out of engagement with the vertical proximal surface of the right-most tooth 54 in FIG. 9. That allow handle 44 to slide to the right in FIG. 9, thereby moving end 80 of control wire 76 to the right and allowing distal end 38 of tube 32 of the catheter to move upward (arrow 71 in FIG. 5) and reduce the curvature of tube 32.

The curvature of the tube may be changed before the catheter enters or leaves the pleural space, or the distal end or the distal end plus some additional portion of the central portion of the catheter may be inserted into the pleural space and the curvature changed after such entry. In any case, the curvature is changed by moving slidable means 44 towards the proximal end (to increse the curvature) or towards distal end 38 (to decrease the curvature).

FIG. 8 is a cross-sectional view of the catheter showing gutter 42, which is integrally formed with the tube, having slidable control wire 76 inside. FIGS. 10, 11, and 12 show alternate schemes for mounting the control wire. In FIG. 10, gutter 42 is located on the inner surface of wall 32. In FIG. 11, there is no separate gutter for control wire 76. Because wall 32 is thick enough, control wire 76 is located in a longitudinal passageway in wall 32. FIG. 12 shows an embodiment (discussed below) in which two control wires 76 are used, each in its own gutter 42 located on the outer surface of wall 32.

FIG. 13 shows a catheter in which two control wires 76 are mounted in gutters 42, each of which gutter extends along most of the length of wall 32. As shown in the transverse cross-sectional view of FIG. 12, the two gutters 42 are substantially oppositely disposed on the outer surface of wall 32, that is, one gutter may be thought of as being at 0° and the other gutter at 180°. This configuration may be useful in a case in which distal end 38 of the catheter must be able to be moved up and down (and the curvature of the tube changed from concave up to concave down) without rotating the catheter within the patient. Downward movement of distal end 38 as shown in FIG. 14 is accomplished by pulling lower control wire 76 towards the proximal end of the catheter. Upward movement of distal end 38 (shown in broken line in FIG. 14) is accomplished by pulling upper control wire 76 towards the proximal end of the catheter.

FIG. 15 shows a catheter having one control wire 76 in one gutter 42 activated by rotatable control means 90. Instead of sliding between the distal and proximal ends of the catheter as in previous embodiments, the control means of FIGS. 15, 16, and 17 does not move longitudinally along the tube but rather rotates clockwise or counterclockwise.

Rotatable control means 90 comprises barrel 92 having a knurled outer surface 94 (for better gripping), and depressions or notches 98 located on proximal flat end 96 of barrel 92. Detent 100, which is integral with collar 102, fits into whichever notch 98 is topmost (considering the top of the catheter to be where gutter 42 is located) to prevent rotatable control 90 from undesirable rotation.

FIG. 16 is a partial longitudinal cross-sectional view of control means 90 on wall 32 of the catheter. Control means 90 is prevented from moving towards the proximal end of the device (to the left in FIGS. 15 and 16) by its engagement with detent 100, which is integral with collar 102. Control means 90 is kept from moving to the right in FIG. 15 and 16, that is, towards distal end 38, by the abutment of internal member 106 of the control means against the proximal end of gutter 42 and against block 114, which is located on the outer surface of the tube of the catheter 180° away from gutter 42.

Control wire 76 passes out the proximal end of gutter 42 and up into passageway 108 between the sloping surface of internal member 106, which rotates as part of control means 90, and the sloping surface of non-rotatable collar 102, which is fixed to the outer surface of the catheter tube. End 80 of wire 76 is embedded in block 112 (FIGS. 16 and 17) and is held in place by pin 110. As control means 90 is rotated in either direction, end 80 of control wire 76 is moved farther away from the proximal end of gutter 42, thereby pulling control wire 76 to the left in FIG. 16. As with previous embodiments, pulling control wire 76 towards the proximal end of the device brings the distal end of the wire towards the proximal end of the device, which in turn pulls distal end 38 of the catheter towards the proximal end of the catheter.

In FIG. 5, because gutter 42 was located on the bottom of wall 32 of the catheter, pulling the control wire towards the proximal end of the device caused distal end 38 of the catheter to move downward as shown by arrow 70 in FIG. 5. In the embodiment of FIGS. 15, 16, and 17, because gutter 42 is located along the top of the tube of the catheter, pulling control wire 76 to the left in FIGS. 15 and 16, that is, towards the proximal end of the device, will move distal end 38 towards the proximal end of the device by moving distal end 38 up in the direction shown by arrow 128. Arrow 130 in FIG. 17 indicates that rotatable control means 90 may be rotated in either direction. As will be understood, rotation in either direction from the position shown in FIGS. 15 and 16 will pull control wire 76 towards the proximal end of the device. Reducing the curvature of the device by moving the proximal end of control wire 76 towards the distal end of the device requires rotating control means 90 in a direction opposite to that used to pull control wire 76 towards the proximal end of the device.

Another embodiment of the device of this invention is shown in FIGS. 18-21. The control means comprises two split body parts 47, which can slide with respect to one another at interface 122 by means of two longitudinal bulbous guide runners 118 each located within a mating longitudinal concavity 120. FIG. 19, which is taken along line 19—19 of FIG. 18, shows that each of the two split body parts 47 of the handle has one longitudinal guide runner 118 on one side and one mating concavity 120 on the other side. Each split body part 47 has its own curved handle portion 50 defining finger hole 48. Each split body part 47 has its own control wire 76 located within its own gutter 42 having proximal end 82 (FIG. 20). End 80 of each control wire 76 is attached to split body part 47 by its respective pin 110.

To change the curvature of the catheter the two slidable handle parts 47 are moved in opposite directions as shown in FIG. 21. For example, lower split body part 47 is moved to the left, thereby pulling control wire 76 located in lower gutter 42 to the left, in the direction shown by arrow 126. At the same time, upper split body part 47 of the handle is moved to the right, thereby allowing control wire 76 in upper gutter 42 to move to the right in the direction shown by arrow 124. The combined opposite movements of the two control wires cause distal end 38 of the catheter to move downward. The catheter may be restored to its straight orientation (as in FIG. 18) or brought to a position in which the curvature of the device is upward by reversing the directions of movement of the two handle portions 47, that is, upper handle portion 47 is moved to the left and lower handle portion 47 is moved to the right.

In this embodiment, there is no separate means such as ratchet means 52 in the embodiment of FIG. 4 or detent 100 in the embodiment of FIG. 15 to lock the position of the two control wires after the two split body parts 47 have been moved apart. Instead, the two control wires 76 are maintained in position with respect to one another by the friction fit at interface 122, including the friction fit between the two bulbous guide runners 118 and their mating bulbous concavities 120. The two split body parts 47 are also friction fit onto tube 32 itself to prevent them from moving easily with respect to the tube.

FIG. 22 shows the simple construction of an embodiment in which a slidable member is used to pull control wire 76. Slidable member (control means) 132 is essentially a cylinder larger in diameter than the diameter of the tube of the catheter. The only two internal members of slidable control member 132 are block 134, in which end 80 of control wire 76 is embedded, and tooth 136, which is triangular in cross-section and slides up and over each of the four ratchet teeth 54 as slidable control member 132 is moved to the left.

In this embodiment, the elasticity of the material from which slidable member 132 and tooth 136 are made allows some deformation so that tooth 136 is able to clear each of teeth 54. However, in contrast to the embodiment shown, for example, in FIG. 4, there is no separate release means to allow tooth 136 to slide back to the right and up and over each of teeth 54. Thus, slidable member 132 provides simplified construction as compared to many of the other embodiments disclosed herein. To unlock tooth 136 to allow it to slide to the right in FIG. 22 after it has passed over and been locked to the left of any of teeth 54, slidable member 132 is squeezed on its sides to increase the spacing between the top of the slidable member and the tube and thereby to maximize the spacing between tooth 136 and teeth 54. Slidable member 132 is then pulled to the right and tooth 136 is forced over teeth 54. The materials of construction should be such as to allow the teeth to be pulled apart rapidly and without excessive force.

FIG. 23 shows another embodiment in which cylindrical slidable member 138 is used to pull control wire 76. Four semicircular bands or collars 140 for different curvatures are fixedly attached to the outer surface of wall 32 of the catheter. End 80 of control wire 76 is connected to block 134. Member 138 is pulled towards the proximal end of the device and slides over collars 140. Member 138 is made of a resilient material and circular end 142 of member 138 contracts slightly after a collar 140 slides out from under member 138. The contraction of slidable member 138 at both of its ends is shown to an exaggerated degree in FIG. 23. Member 138 is prevented from being pulled towards the distal end of the device by the abutment of circular end 142 against collar 140. To relieve the tension on control wire 76 and permit the curvature of the catheter to decrease, slidable member 138 is forced towards the distal end of the catheter up and over collar 140 (to the right in FIG. 23).

Variations and modifications will be apparent to those skilled in the art and the claims are intended to cover all such variations and modifications that fall within the true spirit and scope of the invention. For example, any material of construction may be used so long as it is medically acceptable, has the required physical properties (e.g., strength, resilience, flexibility), and can be satisfactorily sterilized. The control means for adjusting the curvature of the catheter may also be made of any acceptable material that can be sterilized and will usually be made of the same material as for the rest of the catheter. The control wire may be a plastic filament, for example, of nylon, or it may be a metal wire. To avoid interfering with X-rays, a non-metallic substance for the control wire may be preferred. The catheter itself may have a radio-opaque line. Indicia 40 (FIG. 4) may also be radio-opaque and large enough to be legible in an X-ray. Obviously the embodiments herein and the claims need not be restricted to catheters for the pleural cavity. Furthermore, the patient may be an animal, not just a human being.

I claim:

1. A thoracic catheter consisting essentially of (a) an elongate flexible tube for the passage of fluid into or out of the thoracic cavity of a patient, the tube having a wall, a distal end and an elongate portion for insertion into the thoracic cavity of the patient, and a proximal end that remains outside the patient, (b) control means connected to the tube for changing the curvature of at least 60% of the elongate portion of the tube that is designed to be inserted into the thoracic cavity of the patient to facilitate positioning of the distal end and the elongate portion of the tube in the thoracic cavity of the patient, (c) means defining an elongated passageway and at least one control wire having a distal end and a proximal end and extending along at least part of the length of the tube inside the means defining an elongated passageway the distal end of the at least one wire being closer to the distal end of the catheter and the proximal end of the at least one wire being closer to the proximal end of the tube, wherein the distal end of the at least one control wire is attached to the tube so that when the proximal end of the at least one wire is pulled towards the proximal end of the tube, the distal end of the tube is pulled towards the proximal end of the tube, thereby changing the curvature of at least 60% of the elongate portion of the tube that is designed to be inserted into the thoracic cavity of the patient, and (d) means for temporarily maintaining the curvature of the tube.

2. The catheter of claim 1 in which the control means includes a member slidably mounted on the tube nearer to the proximal end of the tube than to the distal end of the tube and the proximal end of the at least one control wire that is attached to the tube is attached to the slidably mounted ember so that as the slidably mounted member is moved towards the proximal end of the tube, the distal end of the at least one wire is pulled towards the proximal end of the tube, thereby changing the curvature of at least 80% of the elongate portion of the tube that is designed to be inserted into the thoracic cavity of the patient.

3. The catheter of claim 2 in which the wall of the tube defines the elongate passageway and the at least one control wire that is attached to the tube and to the slidably mounted member is carried within the passageway.

4. The catheter of claim 2 in which the means defining an elongate passageway is a gutter connected to the tube wall or in the tube wall, said gutter defining the elongate passageway in which the at least one control wire that is attached to the tube and to the slidably mounted member is carried.

5. The catheter of claim 4 in which the gutter is on the outer surface of the tube.

6. The catheter of claim 1 in which the control means comprises a member rotatably mounted on the tube nearer the proximal end of the tube and the proximal end of the at least one control wire that is attached to the tube is attached to the rotatably mounted member so that as the rotatably mounted member is rotated with respect to the tube, the distal end of the wire is pulled towards the proximal end of the tube, thereby changing the curvature of at least 80% of the elongate portion of the tube that is designed to be inserted into the thoracic cavity of the patient.

7. The catheter of claim 6 in which the wall of the tube defines the elongate passageway and the at least one control wire that is attached to the tube and to the rotatably mounted member is carried within the passageway.

8. The catheter of claim 6 in which the means defining an elongate passageway is a gutter connected to the tube wall or in the tube wall, said gutter defining the elongate passageway in which the at least one control wire that is attached to the tube and to the rotatably mounted member is carried.

9. The catheter of claim 8 in which the gutter is on the outer surface of the tube.

10. The catheter of claim 1 in which the at least one control wire is two control wires, the first control wire having a distal end and a proximal end and the second control wire having a distal end and a proximal end, the wires extending along at least part of the length of the tube, which has a radius, on substantially opposite radial portions thereof, the distal ends of the wires being closer to the distal end of the tube and the proximal ends of the wires being closer to the proximal end of the tube.

11. The catheter of claim 10 in which the distal end of each control wire is attached to the tube so that when the proximal end of the first wire is pulled towards the proximal end of the tube, the distal end of the tube is pulled towards the proximal end of the tube in a first direction, thereby changing the curvature of at least 80% of the elongate portion of the tube that is designed to be inserted into the thoracic cavity of the patient, and when the proximal end of the second wire is pulled towards the proximal end of the tube, the distal end of the tube is pulled towards the proximal end of the tube in a second direction opposite the first direction, thereby changing the curvature of at least 80% of the elongate portion of the tube that is designed to be inserted into the thoracic cavity of the patient.

12. The catheter of claim 11 in which the control means comprises first and second control members connected to the tube and being slidably mounted with respect to each other and with respect to the tube nearer the proximal rather than distal end of the tube, the proximal end of the first control wire being attached to the first control member and the proximal end of the second control wire being attached to the second control member.

* * * * *